United States Patent [19]

Troxler

[11] 4,080,463
[45] Mar. 21, 1978

[54] 2-SUBSTITUTED-AMINOPROPOXY INDOLES

[75] Inventor: Franz Troxler, Bottmingen, Switzerland

[73] Assignee: Sandoz Ltd., Basel, Switzerland

[21] Appl. No.: 711,905

[22] Filed: Aug. 5, 1976

[30] Foreign Application Priority Data

Aug. 7, 1975 Switzerland ............ 10308/75
Aug. 7, 1975 Switzerland ............ 10309/75

[51] Int. Cl.² ............ A61K 31/40; C07D 209/14; C07D 209/20
[52] U.S. Cl. ............ 424/274; 260/326.14 R; 260/326.15; 260/326.16
[58] Field of Search ............ 260/326.14 R, 326.15; 424/274

[56] References Cited

U.S. PATENT DOCUMENTS 3,471,515  10/1969  Troxler et al. ............ 260/326.15
3,751,429   8/1973  Seeman et al. ............ 260/326.14 R

FOREIGN PATENT DOCUMENTS 105,705  1/1965  Norway ............ 260/326.15

Primary Examiner—Ethel G. Love

Attorney, Agent, or Firm—Gerald D. Sharkin; Robert S. Honor

[57] ABSTRACT

This invention provides compounds of formula I,

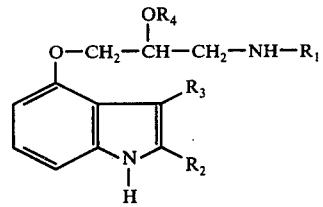

wherein
$R_1$ is alkyl, alkenyl or alkinyl of up to 9 carbon atoms, or 1-ethinylcycloalkyl,
$R_2$ is hydrogen, halogen of atomic number from 17 to 35 or methyl,
$R_3$ is halogen of atomic number from 17 to 35 when $R_2$ is hydrogen or methyl, and is methyl when $R_2$ is halogen of atomic number from 17 to 35, and
$R_4$ is hydrogen or a $R_5Co-$ group wherein $R_5$ is alkyl of 1 to 6 carbon atoms, phenoxy-alkyl, phenyl or substituted phenyl, which are useful, for example, for treating coronary conditions.

18 Claims, No Drawings

2-SUBSTITUTED-AMINOPROPOXY INDOLES

The present invention relates to 4-(3-alkylaminopropoxy)-indole derivatives.

More particularly, this invention provides compounds of formula I,

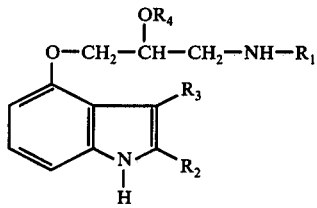

wherein
- $R_1$ is alkyl, alkenyl or alkinyl of up to 9 carbon atoms, in which any multiple bond is in a position other than $\alpha,\beta$ to the nitrogen atom, or a 1-ethinylcycloalkyl of 5 or 6 ring carbon atoms,
- either $R_2$ is hydrogen or methyl, and $R_3$ is halogen of atomic number from 17 to 35,
- or $R_2$ is halogen of atomic number from 17 to 35, and $R_3$ is methyl,
- $R_4$ is hydrogen or $R_5CO—$, wherein $R_5$ is alkyl of 1 to 6 carbon atoms; phenoxyalkyl, the alkyl residue of which is of 2 to 6 carbon atoms and in which the phenyl residue is unsubstituted or monosubstituted with chlorine; phenyl; phenyl mono-, di- or trisubstituted with alkyl of 1 to 4 carbon atoms or alkoxy of 1 to 4 carbon atoms; or phenyl mono- or disubstituted with halogen of atomic number from 9 to 35.

The substituent $R_1$ is preferably a branched residue, especially in the position $\alpha$ to the nitrogen atom to which it is bound. When $R_1$ is alkyl, this is preferably of 1 to 7 carbom atoms, in particular 3 to 5 carbon atoms, especially tert.butyl or isopropyl. When $R_1$ is alkenyl or alkinyl, this is preferably allyl or 1-prop-2-inyl, mono- or disubstituted with alkyl of 1 to 3 carbon atoms, preferably methyl or ethyl, in the position $\alpha$ to the nitrogen atom. When $R_1$ is 1-ethinylcycloalkyl, this is preferably 1-ethinylcyclohexyl.

The substituent $R_4$ is preferably $R_5CO$. $R_5$ is preferably phenyl or substituted phenyl. When the phenyl residue bears more than one substituent, these substituents are preferably identical. When the substituents are halogen substituents, these are preferably chlorine. When the substituents are alkyl or alkoxy, these preferably contain 1 or 2 carbon atoms and especially signify methyl or methoxy. When $R_5$ is alkyl, this is preferably branched, especially in the position $\alpha$ to the carbonyl group, and preferably contains 3 to 5 carbon atoms, especially tert.butyl. When $R_5$ is phenoxyalkyl, the phenoxy residue is preferably monosubstituted by chlorine and the alkyl residue preferably contains 3 to 5 carbon atoms. Preferred such radicals include 2-(p-chlorophenoxy)-2-propyl.

The compounds of formula I can, by virtue of the asymmetric carbon atom in the position $\beta$ to the oxygen atom, exist in the form of optically active isomers or racemates. Of the (R) and (S) enantiomorphs, those which possess the (S)-configuration at the aforementioned carbon atom are preferred.

The invention also provides a process for the production of the compounds of formula I, comprising
a. producing a compound of formula Ia,

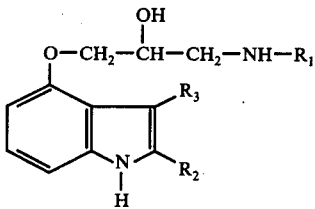

wherein $R_1$, $R_2$ and $R_3$ are as previously defined, by reacting a compound of formula II,

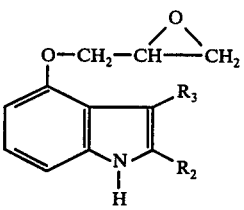

wherein $R_2$ and $R_3$ are as previously defined, or a reactive derivative thereof, with a compound of formula III, $$R_1—NH_2 \qquad \text{III}$$

wherein $R_1$ is as previously defined, or
b. producing a compound of formula Ib,

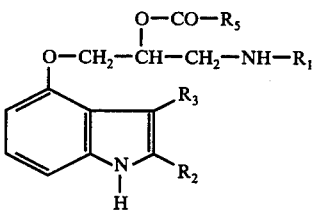

wherein $R_1$, $R_2$, $R_3$ and $R_5$ are as previously defined, by acylating a compound of formula Ia as previously defined.

The reaction of an amine of formula III with a compound of formula II, or a reactive derivative thereof, according to process variant (a), can be effected by the usual methods for the preparation of secondary $\beta$-aminoalcohols from epoxides or derivatives thereof. Suitable reactive derivatives of the compounds of formula II are, for example, compounds carrying instead of the 2,3-epoxy group, a hydroxy group in position 2- of the side chain and a radical capable of being split-off by reaction with an amine in position 3- of the side chain, e.g. addition products of compounds of formula II with compounds of formula HY, wherein Y signifies halogen or a sulphonic acid residue, for example mesyloxy or tosyloxy. The reaction may suitably be effected at a temperature from ca. 20° to ca. 150° C, preferably at the boiling temperature of the reaction mixture. The reaction may suitably be effected in an organic solvent which is inert under the reaction conditions, for example, a cyclic ether, or in an excess of the amine of formula III, if this compound is a liquid.

The acylation of the compounds of formula Ia according to proces variant b) can be effected in manner analogous to known methods for the acylation of secondary alcohols, for example, by reaction with acid anhydrides or halides of the acids of formula $R_5COOH$, wherein $R_5$ is as previously defined, preferably the anhydrides thereof. When the amino group in the aminopropoxy side chain is acylatable, it is desirable to protonate this group prior to the acylation, for example by the addition of an acid, especially the acid $R_5COOH$, or to employ the compound of formula Ia in the form of an acid addition salt, for example, the hydrochloride. When the acylating agent to be used is an acid anhydride, the reaction may, for example, be effected at a temperature between ca. 0° and ca. 100° C, particularly in the presence of an excess of the acid anhydride. With acyl halides, the acylation may preferably be effected either at room temperature or at slightly elevated temperatures.

The process variants of the invention do not alter the configuration of the asymmetrically substituted carbon atom. Accordingly, when racemic starting materials are employed, racemic final products of formula I are obtained, and when optically active starting materials are employed, corresponding optically active final products are obtained.

The resulting compounds of formula I may be isolated and purified using conventional techniques.

Free base forms of the compounds of formula I may be converted into acid addition salt forms and vice versa in conventional manner.

The starting materials of formula II may be obtained by halogenation of compounds of formula IV,

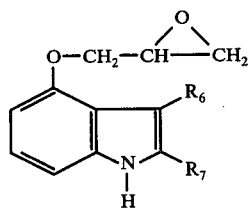
IV wherein either
$R_6$ is methyl and
$R_7$ is hydrogen, or
$R_6$ is hydrogen and
$R_7$ is hydrogen or methyl,
with a compound of formula V,

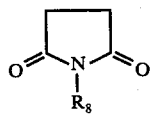
V wherein $R_8$ is halogen of atomic number from 17 to 35.

The reaction may be effected in manner analogous to known methods.

Insofar, as the production of starting materials is not described, these are known or may be produced in accordance with known processes, or in a manner analogous to the process variants described herein or to known processes.

In the following non-limitative Examples all temperatures are indicated in degrees Centigrade and are uncorrected.

EXAMPLE 1

3-tert.Butylamino-1-(3-chloro-2-methyl-4-indolyloxy)-2-propanol ([process a)]

3 g of 3-chloro-4-(2,3-epoxypropoxy)-3-methyl indole is heated in an autoclave with 60 ml of tert. butylamine at 100°, evaporated to dryness, and the dry residue shaken out between tartaric acid and methylene chloride. The base is isolated in conventional manner and the title compound crystallised from methanol. The title compound in the form of crystals containing the crystallisation solvent sinters at ca. 50°.

The 3-chloro-4-(2,3-epoxypropoxy)-3-methyl indole required as starting product is produced as follows:

2.18 g of N-chlorosuccinimide are added to a solution of 3 g of 4-(2,3-epoxypropoxy)-2-methylindole in 25 ml of absolute tetrahydrofuran. The reaction mixture is heated rapidly to boiling, evaporated to dryness and the dry product chromatographed on silica gel whereby the starting material is eluted with methylene chloride.

EXAMPLE 2

3-tert.Butylamino-1-(3-chloro-4-indolyloxy)-2-propanol [process a)]

A solution of 1.13 g of 3-chloro-4-(2,3-epoxypropoxy)indole (prepared in manner analogous to the preparation of the starting material in Example 1, m.p. 107°-110°) and 2.2 g tert.butylamine in 15 ml of dioxan are boiled under reflux for 5 hours, evaporated to dryness and the title compound recrystallised from ether/petroleum ether. M.p. 95°-97°.

In manner analogous to Example 1 or 2, but employing appropriate starting materials in approximately equivalent amounts, the following compounds of formula Ia can be obtained.

| Example | $R_1$ | $R_2$ | $R_3$ | M.P. |
|---|---|---|---|---|
| 3 | —C(CH₃)₃ | Br | CH₃ | 60° (sinters) |
| 4 | —C(CH₃)₃ | Cl | CH₃ | 104 – 108° |
| 5* | —C(CH₃)₃ | CH₃ | Br | 93 – 98° |
| 6* | | CH₃ | Br | Fu⁺: 193 – 196° (Z**) |
| 7 | | CH₃ | Cl | Fu⁺: 197 – 199° (Z**) |
| 8 | | CH₃ | Cl | HFu⁺⁺: 188 – 190° (Z**) |

**with decomposition
⁺bis (base) fumarate form
⁺⁺hydrogen fumarate form
*Starting product produced by the bromination in manner analogous to that for starting materials of Example 1, but at room temperature.

EXAMPLE 9

4-(2-Benzoyloxy-3-tert.butylaminopropoxy)-3-chloro-2-methyl-indole [process b)]

3.1 g of 1-tert.butylamino-3-(3-chloro-2-methyl-indol-4-yloxy)-2-propanol, 6.1 g of benzoic acid and 12 ml of hexamethyl phosphoric acid triamide are heated on a steam bath until all of the benzoic acid is dissolved. After cooling to room temperature, 2.9 g of benzoic acid anhydride are added and stirring is effected for 15 hours. The resulting clear yellow solution is poured onto ice, 250 ml of ether are added and stirring effected for 1 hour. After making the liquid alkaline with concentrated ammonia, the ether phase is separated, shaken out with tartaric acid, made alkaline while cooling with ice, with concentrated ammonia and extracted with methylene chloride. After evaporating the methylene chloride, the residual title compound is crystallised with 1 mol of malonic acid from tetrahydrofuran and ether. M.p. of hydrogen malonate form: 176°–177°.

In manner analogous to Example 9, but employing appropriate starting materials in approximate equivalent amounts, the following compounds of formula Ib can be obtained.

| Ex. | $R_1$ | $R_2$ | $R_3$ | $R_5$ | M.P. |
|-----|-------|-------|-------|-------|------|
| 10 | $-C(CH_3)_3$ | $CH_3$ | Br | $-C(CH_3)_3$ | Fu$^+$: from 186° (Z*) |
| 11 | $\begin{array}{c} CH_2-CH_3 \\ \| \\ -C-C\equiv CH \\ \| \\ CH_2-CH_3 \end{array}$ | $CH_3$ | Cl | $-C(CH_3)_3$ | HCl$^{+++}$: from 140° (frit) |
| 12 | $-C(CH_3)_3$ | $CH_3$ | Cl | $-C(CH_3)_3$ | Fu$^+$:196–199° |
| 13 | $-C(CH_3)_3$ | Cl | $CH_3$ | ⌬ | HMA**: 123–125° |
| 14 | $-C(CH_3)_3$ | Br | $CH_3$ | $-C(CH_3)_3$ | HMA**: 171–173° |

*with decomposition
$^+$bis (base) fumarate form
$^{+++}$hydrochloride form
**hydrogen maleate In manner analogous to Example 9, but employing appropriate starting materials in approximate equivalent amounts, the following compounds of formula Ib can be obtained.

| Ex. | $R_1$ | $R_2$ | $R_3$ | $R_4$ |
|-----|-------|-------|-------|-------|
| 15 | $\begin{array}{c} CH_3 \\ \| \\ CH(CH_2)_5CH_3 \end{array}$ | Cl | $CH_3$ | $CH_3-\bigcirc-CO$ |
| 16 | $\begin{array}{c} CH_3 \\ \| \\ C(CH_2)_3CH_3 \\ \| \\ CH_3 \end{array}$ | Br | $CH_3$ | $\begin{array}{c} OCH_3 \\ \bigcirc-CO \end{array}$ |
| 17 | $CH_2CH_3$ | $CH_3$ | Br | $\begin{array}{c} n-C_3H_7O \\ n-C_4H_9-O-\bigcirc-CO \\ CH_3O \quad OCH_3 \end{array}$ |
| 18 | $\begin{array}{c} C_2H_5 \\ \| \\ C.CH=CH_2 \\ \| \\ CH_3 \end{array}$ | H | Cl | $F-\bigcirc-CO$ |
| 19 | $\begin{array}{c} C_2H_5 \\ \| \\ CH.CH=CH.CH_3 \end{array}$ | $CH_3$ | Br | $\begin{array}{c} Cl \\ \bigcirc-CO \end{array}$ |
| 20 | $\begin{array}{c} C_2H_5 \\ \| \\ CH.CH=CH_2 \end{array}$ | Cl | $CH_3$ | $Br-\bigcirc-CO$ |
| 21 | $\begin{array}{c} C_2H_5 \\ \| \\ C.C\equiv CH \\ \| \\ C_2H_5 \end{array}$ | Cl | $CH_3$ | $\begin{array}{c} Cl \\ \bigcirc-CO \\ Br \end{array}$ |
| 22 | $CH_3$ | H | Cl | $n-C_6H_{13}-CO$ |
| 23 | $n-C_7H_{15}$ | Cl | $CH_3$ | $CH_3-CO$ |
| 24 | $n-C_9C_{19}$ | Br | $CH_3$ | 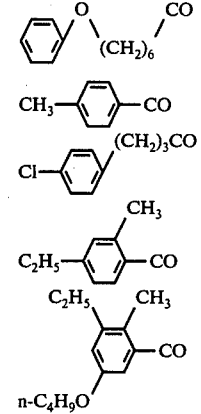 |
| 25 | $CH_2CH=CH_2$ | $CH_3$ | Br | $\bigcirc\!\!\!\begin{array}{c}O\\ \diagdown\\ (CH_2)_6\end{array}\!\!\!\diagup CO$ |
| 26 | $(CH_2)_7CH=CH_2$ | H | Cl | $CH_3-\bigcirc-CO$ |
| 27 | $CH_2C\equiv CH$ | Br | $CH_3$ | $Cl-\bigcirc-(CH_2)_3CO$ |
| 28 | $(CH_2)_3C\equiv C(CH_2)_3CH_3$ | $CH_3$ | Br | $\begin{array}{c} CH_3 \\ C_2H_5-\bigcirc-CO \end{array}$ |
| 29 | $n-C_5H_{11}$ | H | Cl | $\begin{array}{c} C_2H_5 \quad CH_3 \\ \bigcirc-CO \\ n-C_4H_9O \end{array}$ |

The compounds of formula I are useful because they possess pharmacological activity in animals. In particular, the compounds are useful as β-adrenoceptor blocking agents, e.g. for the prophylaxis and therapy of coronary diseases, particularly in the treatment of Angina pectoris, in the hyperkinetic heart syndrome and conditions resulting from muscular hypertrophic subvalvular aortic stenosis, as indicated in standard tests, e.g. by an inhibition of the positive inotropic adrenaline effect in the spontaneously beating guinea pig atrium at a bath concentration of from 0.005 to 3 mg/liter in accordance with the method of K. Sammeli, Helv. Physiol. Acta. 25 CR 215–221 (1967); and in the infusion test in narcotized cats at doses of approximately 0.02 to 1 mg/kg i.v., where they induce a strong, long lasting inhibition of the tachycardia and blood pressure lowering caused by isoproterenol.

For the abovementioned use, the dosage administered will, of course, vary depending on the compound employed, mode of administration and treatment desired. However, in general, satisfactory results are obtained with a daily dosage of from about 0.01 to about 1.5 mg/kg animal body weight, conveniently given in divided doses 2 to 4 times a day or in sustained release form. For the larger mammal, the total daily dosage is in the range of from about 1 to about 500 mg, and dosage forms suitable for oral administration comprise from about 0.25 to about 250 mg of the compound, admixed with a solid or liquid pharmaceutical carrier or diluent.

The compounds are furthermore useful as inhibitors of the increase in serum fatty acids induced by emotional stress and also as agents for the treatment and prophylaxis of myocardism as indicated in standard tests for showing inhibition of increased free fatty acid concentration due to mobilisation, and lipolysis, in blood, induced by emotional stress; for example, by an inhibition of glycerol release stimulated by isoproterenol (i) in vitro, e.g. at a concentration of about 0.1 to about 10 mg/l solution of the compounds in fat cells of the epididymal fat tissue of rats, the cells having been isolated in accordance with the method of M. Rodbell [J. Biol. Chem. 239, 375–80 (1964)] and ii) in vivo, e.g. in rats on s.c. administration of from about 0.1 to about 1 mg/kg animal body weight of the compounds.

The compounds are furthermore useful as inhibitors of hyperglycemia induced by emotional stress and therefore as suppressants of appetite induced by emotional stress, as indicated in standard tests, e.g. by an inhibition of glucose release stimulated by isoproterenol in rats in vivo on s.c. administration of from about 0.1 to 1 mg/kg of animal body weight of the compounds.

For the abovementioned emotional stress uses for stress conditions the dosages will, of course, vary depending on the compound employed, mode of administration and treatment desired. However, in general, satisfactory results are obtained with a daily dosage of from about 0.02 to about 5 mg/kg animal body weight, conveniently given in divided doses 2 to 4 times a day or in sustained release form. For the larger mammal, the total daily dose is in the range of from about 1 to about 100 mg and dosage forms suitable for oral administration comprise from about 0.25 to about 50 mg of the components admixed with a solid or liquid pharmaceutical carrier or diluent.

The compounds are furthermore useful as antiarrhythmic agents, e.g. for the treatment of heart rhythm disorders, as indicated in standard tests, for example by a protection against cardiac arrhythmia induced by chloroform in mice on i.p. administration of from 10 to 50 mg/kg animal body weight of the compounds in accordance with the principles of J. W. Lawson [J. Pharmacol. Exp. Therap. (1968) 160,22–31].

For this use the dosage will, of course, vary depending on the compound employed, mode of administration and treatment desired. However, in general, satisfactory results are obtained with a daily dosage of from about 0.1 to 50 mg/kg animal body weight, conveniently given in divided doses 2 to 4 times a day or in sustained release form. For the larger mammal, the total daily dosage is in the range of from about 5 to 200 mg and dosage forms suitable for oral administration comprise from about 1 to 50 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include orgnic acid salt forms such as the maleate, hydrogen maleate, fumarate, hydrogen fumarate, malonate, hydrogen malonate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutically acceptable carrier or diluent. Such compositions conveniently contain more than 1% by weight of the compound of formula I and may be in such forms as capsules.

What is claimed is:

1. A compound of formula I,

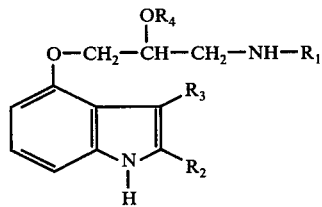

I wherein
$R_1$ is alkyl, alkenyl or alkinyl of up to 9 carbon atoms, in which any multiple bond is in a position other than $\alpha,\beta$ to the nitrogen atom, or a 1-ethinylcycloalkyl of 5 or 6 ring carbon atoms, either
$R_2$ is hydrogen or methyl, and
$R_3$ is halogen of atomic number from 17 to 35, or
$R_2$ is halogen of atomic number from 17 to 35, and
$R_3$ is methyl,
$R_4$ is hydrogen or $R_5CO$—, wherein $R_5$ is alkyl of 1 to 6 carbon atoms; phenoxyalkyl, the alkyl residue of which is of 2 to 6 carbon atom and in which the phenyl residue is unsubstituted or monosubstituted with chlorine; phenyl; phenyl mono-, di- or trisubstituted with alkyl of 1 to 4 carbon atoms or alkoxy of 1 to 4 carbon atoms; or phenyl mono- or disubstituted with halogen of atomic number from 9 to 35, or a pharmaceutically acceptable acid addition salt form thereof.

2. A compound of claim 1 which is 4-(2-benzoyloxy-3-tert.butylaminopropoxy)-3-chloro-2-methylindole.

3. A pharmaceutical composition for the treatment of heart rhythm disorders comprising an antiarrhythmic effective amount of a compound of claim 1, in free base form or in pharmaceutically acceptable acid addition salt form, in association with a pharmaceutically acceptable diluent or carrier.

4. A method of treating heart rhythm disorders in animals which comprises administering to an animal in need of such treatment a anti-heart rhythm disorder effective amount of a compound of claim 1.

5. A compound of claim 1 which is 3-tert.butylamino-1-(3-chloro-4-indolyloxy)-2-propanol.

6. A compound of claim 1 wherein $R_1$ is —C(CH$_3$)$_3$, $R_2$ is Br, $R_3$ is CH$_3$ and $R_4$ is hydrogen.

7. A compound of claim 1 wherein $R_1$ is —C(CH$_3$)$_3$, $R_2$ is Cl, $R_3$ is CH$_3$ and $R_4$ is hydrogen.

8. A compound of claim 1 wherein $R_1$ is —C(CH$_3$)$_3$, $R_2$ is CH$_3$, $R_3$ is Br and $R_4$ is hydrogen.

9. A compound of claim 1 wherein $R_1$ is

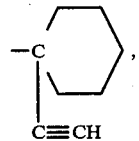

$R_2$ is CH$_3$, $R_3$ is Br and $R_4$ is hydrogen.

10. A compound of claim 1 wherein $R_1$ is

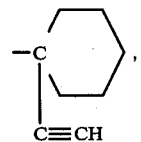

$R_2$ is CH$_3$, $R_3$ is Cl and $R_4$ is hydrogen.

11. A compound of claim 1 wherein $R_1$ is

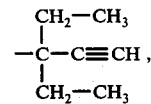

$R_2$ is CH$_3$, $R_3$ is Cl and $R_4$ is hydrogen.

12. A compound of the formula

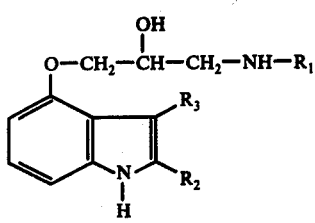

wherein $R_1$, $R_2$, and $R_3$ are as defined in claim 1.

13. A compound of the formula

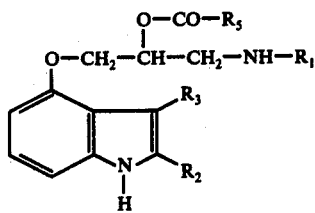

wherein
$R_1$, $R_2$, and $R_3$ are as defined in claim 1; and
$R_5$ represents alkyl of 1-6 carbon atoms; phenoxyalkyl, the alkyl residue of which is of 2-6 carbon atoms and in which the phenyl residue is unsubstituted or mono-substituted with chlorine; phenyl; phenyl mono-, di- or tri-substituted with alkyl of 1-4 carbon atoms or alkoxy of 1-4 carbon atoms; or phenyl mono- or di-substituted with halogen of atomic number from 9 to 35.

14. A compound of claim 13 wherein $R_1$ is $-C(CH_3)_3$, $R_2$ is $CH_3$, $R_3$ is Br and $R_5$ is $-C(CH_3)_3$.

15. A compound of claim 13 wherein $R_1$ is

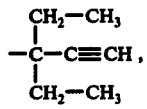

$R_2$ is $CH_3$, $R_3$ is Cl and $R_5$ is $-C(CH_3)_3$.

16. A compound of claim 13 wherein $R_1$ is $-C(CH_3)_3$, $R_2$ is $CH_3$, $R_3$ is Cl and $R_5$ is $-C(CH_3)_3$.

17. A compound of claim 13 wherein $R_1$ is $-C(CH_3)_3$, $R_2$ is Cl, $R_3$ is $CH_3$ and $R_5$ is

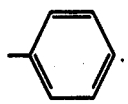

18. A compound of claim 13 wherein $R_1$ is $-C(CH_3)_3$, $R_2$ is Br, $R_3$ is $CH_3$ and $R_5$ is $-C(CH_3)_3$.

* * * * *